United States Patent [19]

Saito et al.

[11] Patent Number: 4,906,400
[45] Date of Patent: Mar. 6, 1990

[54] SMETIC LIQUID CRYSTAL COMPOUND

[75] Inventors: Shinichi Saito; Kisei Kitano; Kazutoshi Miyazawa; Kouji Ohno; Hiromichi Inoue; Makoto Ushioda, all of Ichiharashi, Japan

[73] Assignee: Chisso Corporation, Japan

[21] Appl. No.: 200,050

[22] Filed: May 27, 1988

[30] Foreign Application Priority Data

Jun. 1, 1987 [JP] Japan ................... 62-137884

[51] Int. Cl.$^4$ ................... C09K 19/34; C07D 239/00
[52] U.S. Cl. ................... 252/299.61; 252/299.5; 544/298
[58] Field of Search ................... 544/298; 252/299.5, 252/299.6, 299.61, 299.62, 299.63, 299.64, 299.65, 299.66, 299.67

[56] References Cited

U.S. PATENT DOCUMENTS

| | | | |
|---|---|---|---|
| 4,564,694 | 1/1986 | Hirai et al. | 544/298 |
| 4,621,901 | 11/1986 | Petrzilka et al. | 544/298 |
| 4,632,515 | 12/1986 | Gray et al. | 544/298 |
| 4,683,078 | 7/1987 | Sugimori et al. | 544/298 |
| 4,709,030 | 11/1987 | Petrzilka et al. | 544/298 |
| 4,752,414 | 6/1988 | Eidenschink et al. | 544/298 |

FOREIGN PATENT DOCUMENTS

| | | | |
|---|---|---|---|
| 193191 | 9/1986 | European Pat. Off. | 544/298 |
| 256670 | 2/1988 | European Pat. Off. | 544/298 |
| 257457 | 3/1988 | European Pat. Off. | 544/298 |
| 260077 | 3/1988 | European Pat. Off. | 544/298 |
| 3515374 | 11/1986 | Fed. Rep. of Germany | 544/298 |
| 2292766 | 12/1987 | Japan | 544/298 |
| 2292768 | 12/1987 | Japan | 544/298 |
| 2294664 | 12/1987 | Japan | 544/298 |
| 3005084 | 1/1988 | Japan | 544/298 |
| 3037187 | 2/1988 | Japan | 544/298 |
| 3060972 | 3/1988 | Japan | 544/298 |
| 3063664 | 3/1988 | Japan | 544/298 |
| 7890 | 12/1987 | PCT Int'l Appl. | 544/298 |

OTHER PUBLICATIONS

Furukawa et al, Chem. Abst. 105–52274y (1986) "Ferroelectric Chiral Smectic Liquid Crystal Composition".
Furukawa et al, Chem. Abst. 106–129478y (1987) "Ferroelectric Chiral Smectic Liquid Crystal . . . ".
Hopf et al, Chem. Abst. 106–93764x (1987) "Smectic Liquid-Crystal Phases".

*Primary Examiner*—Mukund J. Shah
*Assistant Examiner*—Cecilia Shen
*Attorney, Agent, or Firm*—Leydig, Voit & Mayer

[57] ABSTRACT

A novel smectic C liquid crystal compound useful as a component of ferroelectric liquid crystal materials capable of effecting high-speed response is provided, which compound is a smectic liquid crystalline 5-alkoxy-2-(4-alkylphenyl)pyrimidine compound expressed by the formula

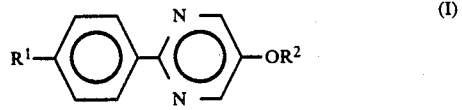

(I)

wherein $R^1$ represents a linear alkyl group of 4 to 20 carbon atoms and $R^2$ represents a linear alkyl group of 7 to 20 carbon atoms.

4 Claims, No Drawings

}

SMETIC LIQUID CRYSTAL COMPOUND

BACKGROUND OF THE INVENTION

This invention relates to a novel smectic liquid crystal compound suitable as a component of ferroelectric liquid crystal materials.

At present, the TN (Twisted Nematic) display mode has been most broadly employed for liquid crystal display elements. This TN display mode has a number of advantages such as low driving voltage, small power consumption, etc., but it is still inferior in the aspect of the response rate to emissive display elements such as cathode ray tubes, electroluminescence displays, plasma displays, etc. A novel TN display element having a twist angle elevated to 180° to 270° has also been developed, but its response rate is still inferior. Efforts for various improvements have been made as described above, but a TN mode display element having a high response rate has not yet been realized. However, in the case of a novel display mode using a ferroelectric liquid crystal the research of which mode has recently been extensively made, there is a possibility of notable improvement in the response rate (see Clark et al, Applied Phys. Lett., 36, 899 (1980)). This mode utilizes chiral smectic phases exhibiting ferroelectric properties such as chiral smectic C phase (hereinafter abbreviated to SC*). It has been known that phases exhibiting ferroelectric properties are not only limited to SC* phase, but also include phases of chiral smectic F, G, H, I, etc.

Various specific features have been required for ferroelectric liquid crystal materials used for ferroelectric liquid crystal display elements practically used, but at present, there is no single compound which satisfies such requirements; hence it is necessary to use ferroelectric liquid crystal compositions obtained by blending some liquid crystal compounds and/or non-liquid-crystalline compounds.

Further, not only have ferroelectric liquid crystal compositions composed only of ferroelectric liquid crystal compounds been reported, but also it has been reported in Japanese patent application laid-open No. Sho 61-195187/1986 that when one or more kinds of compounds exhibiting ferroelectric liquid crystal phases are blended with compounds or compositions exhibiting achiral smectic C, F, G, H, I phase or the like (hereinafter abbreviated to SC phase or the like) as base substances, the resulting blend can constitute a ferroelectric liquid crystal composition as a whole.

Further, it has also been reported that using a compound or a composition containing the compound each exhibiting Sc phase or the like as a base substance, at least one compound which is optically active but exhibits no ferroelectric liquid crystal phase is mixed with the above compound or composition to constitute a ferroelectric liquid crystal composition as a whole (see Mol. Cryst. Liq. Cryst. 89, 327 (1982)).

In a brief summary of these facts, it is seen that when one or more kinds of optically active compounds are blended with base substances, the resulting blend can constitute a ferroelectric liquid crystal composition irrespective of whether or not the optically active compounds exhibit ferroelectric liquid crystal phases.

As such base substances, various compounds exhibiting achiral smectic liquid crystal phases such as the Sc phase or the like may be used, but practically, liquid crystal compounds exhibiting smectic C phases within a broad temperature range including room temperature or mixtures thereof are preferred. Examples of components of these smectic C liquid crystal mixtures are liquid crystal compounds of phenylbenzoates, Schiff's bases, biphenyls, phenylpyridines, 5-alkyl-2-(4-alkoxyphenyl)pyrimidines, etc.

For example, Japanese patent application laid-open No. Sho 61-291679/1986 and WO 86/06401 disclose that mixtures of 5-alkyl-2-(4-alkoxyphenyl)pyrimidine compounds having Sc phase with optically active compounds are used as a ferroelectric liquid crystal material.

SUMMARY OF THE INVENTION

The object of the present invention is to provide a novel smectic C liquid crystal compound useful as a component of ferroelectric liquid crystal materials capable of effecting a high-speed response The present invention resides in a smectic liquid crystalline 5-alkoxy-2-(4-alkylphenyl)pyrimidine compound expressed by the formula

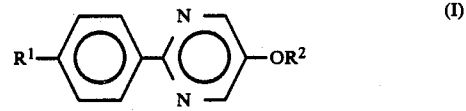
(I)

wherein $R^1$ represents a linear alkyl group of 4 to 20 carbon atoms and $R^2$ represents a linear alkyl group of 7 to 20 carbon atoms.

DETAILED DESCRIPTION OF PREFERRED EMBODIMENTS

The compound of the formula (I) may be prepared through the following route:

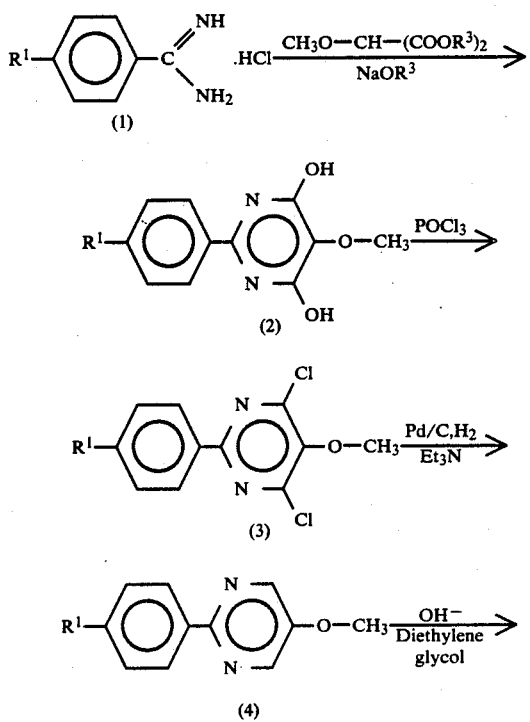

-continued

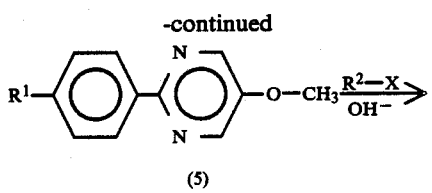

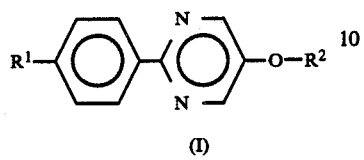

In the above equations, $R^3$ represents an alkyl group such as methyl, ethyl, etc. and X represents a group to be eliminated such as chlorine, bromine, iodine, p-toluenesulfonyloxy group, benzenesulfonyloxy group, methanesulfonyl group, etc.

Namely, a p-alkylbenzamidine hydrochloride (1) is reacted with a methoxymalonic acid diester in the presence of a sodium alcoholate to prepare a diol (2), followed by halogen-substituting the diol with a halogenating agent such as phosphorus oxychloride to obtain a compound (3), dehalogenating it in the presence of a base to obtain a compound (4), heat-treating it in diethylene glycol in the presence of an alkali to obtain a compound (5) and etherifying it to obtain a compound (I).

Further, the compound of the formula (I) may also be prepared through the following route:

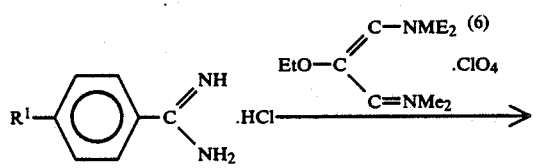

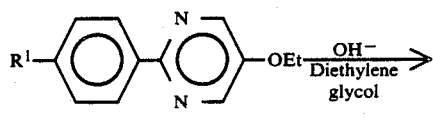

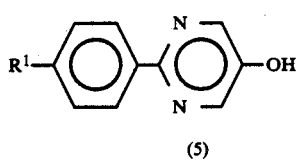

Namely, a p-alkylbenzamidine hydrochloride (1) is reacted with a compound (6) disclosed in a literature (Collection Czechoslov. Chem. Commun., 38 (1973), 1168) in the presence of a sodium alcoholate to obtain a compound (7), which is then treated with an alkali to prepare a compound (5), which is converted into a compound (I) according to the last step of the first route.

As the compound of the present invention, the following 5-alkoxy-2-(alkylphenyl)pyrimidine compounds are examples:
5-heptyloxy-2-(4-butylphenyl)pyrimidine
5-heptyloxy-2-(4-pentylphenyl)pyrimidine 5-heptyloxy-2-(4-hexylphenyl)pyrimidine $C \xrightarrow{32.5} S_C \xleftarrow{50.6} S_A \xleftarrow{76.6} I$ 5-heptyloxy-2-(4-heptylphenyl)pyrimidine $C \xrightarrow{32.2} S_C \xleftarrow{45.0} S_A \xleftarrow{77.5} I$ 5-heptyloxy-2-(4-octylphenyl)pyrimidine

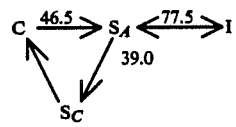

5-heptyloxy-2- (4-nonylphenyl) pyrimidine
5-heptyloxy-2-(4-decylphenyl)pyrimidine
5-heptyloxy-2-(4-undecylphenyl)pyrimidine
5-heptyloxy-2-(4-dodecylphenyl)pyrimidine
5-heptyloxy-2-(4-tridecylphenyl)pyrimidine
5-heptyloxy-2-(4-tetradecylphenyl)pyrimidine
5-octyloxy-2-(4-butylphenyl)pyrimidine
5-octyloxy-2-(4-pentylphenyl)pyrimidine 5-octyloxy-2-(4-hexylphenyl)pyrimidine $C \xrightarrow{27.0} S_C \xleftarrow{67.5} S_A \xleftarrow{84.2} I$ 5-octyloxy-2-(4-heptylphenyl)pyrimidine $C \xrightarrow{30.8} S_C \xleftarrow{64.0} S_A \xleftarrow{84.4} I$ 5-octyloxy-2-(4-octylphenyl)pyrimidine $C \xrightarrow{38.4} S_C \xleftarrow{54.8} S_A \xleftarrow{83.6} I$ 5-octyloxy-2-(4-nonylphenyl)pyrimidine $C \xrightarrow{35.5} S_C \xleftarrow{53.0} S_A \xleftarrow{84.5} I$ 5-octyloxy-2-(4-decylphenyl)pyrimidine $C \xrightarrow{31.7} S_C \xleftarrow{43.0} S_A \xleftarrow{82.8} I$ 5-octyloxy-2-(4-undecylphenyl)pyrimidine
5-octyloxy-2-(4-dodecylphenyl)pyrimidine
5-octyloxy-2-(4-tridecylphenyl)pyrimidine
5-octyloxy-2-(4-tetradecylphenyl)pyrimidine
5-nonyloxy-2-(4-butylphenyl)pyrimidine
5-nonyloxy-2-(4-pentylphenyl)pyrimidine 5-nonyloxy-2-(4-hexylphenyl)pyrimidine $C \xrightarrow{47.7} S_C \xleftarrow{77.2} S_A \xleftarrow{83.6} I$ 5-nonyloxy-2-(4-heptylphenyl)pyrimidine $C \xrightarrow{34.2} S_C \xleftarrow{76.3} S_A \xleftarrow{85.1} I$ 5-nonyloxy-2-(4-octylphenyl)pyrimidine $C \xrightarrow{40.5} S_C \xleftarrow{76.0} S_A \xleftarrow{84.6} I$ 5-nonyloxy-2-(4-nonylphenyl)pyrimidine

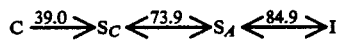

5-nonyloxy-2-(4-decylphenyl)pyrimidine

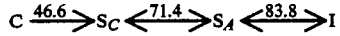

5-nonyloxy-2-(4-undecylphenyl)pyrimidine
5-nonyloxy-2-(4-dodecylphenyl)pyrimidine
5-nonyloxy-2-(4-tridecylphenyl)pyrimidine
5-nonyloxy-2-(4-tetradecylphenyl)pyrimidine
5-decyloxy-2-(4-butylphenyl)pyrimidine
5-decyloxy-2-(4-pentylphenyl)pyrimidine 5-decyloxy-2-(4-hexylphenyl)pyrimidine

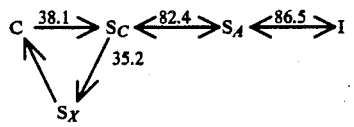

5-decyloxy-2-(4-heptylphenyl)pyrimidine

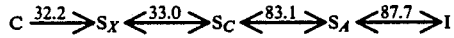

5-decyloxy-2-(4-octylphenyl)pyrimidine

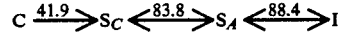

5-decyloxy-2-(4-nonylphenyl)pyrimidine

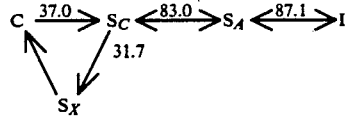

5-decyloxy-2-(4-decylphenyl)pyrimidine

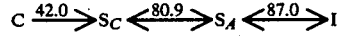

5-decyloxy-2-(4-undecylhenyl)pyrimidine
5-decyloxy-2-(4-dodecylphenyl)pyrimidine
5-decyloxy-2-(4-tridecylphenyl)pyrimidine
5-decyloxy-2-(4-tetradecylphenyl)pyrimidine
5-undecyloxy-2-(4-butylphenyl)pyrimidine
5-undecyloxy-2-(4-pentylphenyl)pyrimidine 5-undecyloxy-2-(4-hexylphenyl)pyrimidine

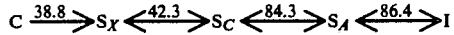

5-undecyloxy-2-(4-heptylphenyl)pyrimidine

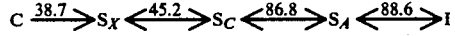

5-undecyloxy-2-(4-octylphenyl)pyrimidine

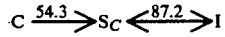

5-undecyloxy-2-(4-nonylphenyl)pyrimidine

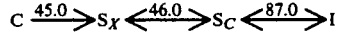

5-undecyloxy-2-(4-decylphenyl)pyrimidine

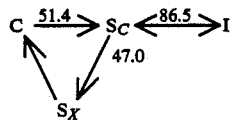

5-undecyloxy-2-(4-undecylphenyl)pyrimidine
5-undecyloxy-2-(4-dodecylphenyl)pyrimidine
5-undecyloxy-2-(4-tridecylphenyl)pyrimidine
5-undecyloxy-2-(4-tetradecylphenyl)pyrimidine
5-dodecyloxy-2-(4-butylphenyl)pyrimidine
5-dodecyloxy-2-(4-pentylphenyl)pyrimidine 5-dodecyloxy-2-(4-hexylphenyl)pyrimidine

5-dodecyloxy-2-(4-heptylphenyl)pyrimidine

5-dodecyloxy-2-(4-octylphenyl)pyrimidine

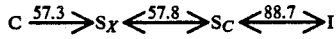

5-dodecyloxy-2-(4-nonylphenyl)pyrimidine

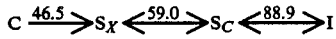

5-dodecyloxy-2-(4-decylphenyl)pyrimidine

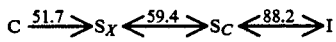

5-dodecyloxy-2-(4-undecylphenyl)pyrimidine
5-dodecyloxy-2-(4-dodecylphenyl)pyrimidine
5-dodecyloxy-2-(4-tridecylphenyl)pyrimidine
5-dodecyloxy-2-(4-tetradecylphenyl)pyrimidine
5-tridecyloxy-2-(4-butylphenyl)pyrimidine
5-tridecyloxy-2-(4-pentylphenyl)pyrimidine 5-tridecyloxy-2-(4-hexylphenyl)pyrimidine

5-tridecyloxy-2-(4-heptylphenyl)pyrimidine 5-tridecyloxy-2-(4-octylphenyl)pyrimidine

5-tridecyloxy-2-(4-nonylphenyl)pyrimidine

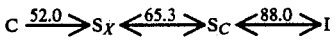

5-tridecyloxy-2-(4-decylphenyl)pyrimidine
5-tridecyloxy-2-(4-undecylphenyl)pyrimidine
5-tridecyloxy-2-(4-dodecylphenyl)pyrimidine
5-tridecyloxy-2-(4-tridecylphenyl)pyrimidine
5-tridecyloxy-2-(4-tetradecylphenyl)pyrimidine
5-tetradecyloxy-2-(4-butylphenyl)pyrimidine
5-tetradecyloxy-2-(4-pentylphenyl)pyrimidine 5-tetradecyloxy-2-(4-hexylphenyl)pyrimidine

5-tetradecyloxy-2-(4-heptylphenyl)pyrimidine 5-tetradecyloxy-2-(4-octylphenyl)pyrimidine

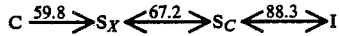

5-tetradecyloxy-2-(4-nonylphenyl)pyrimidine
5-tetradecyloxy-2-(4-decylphenyl)pyrimidine
5-tetradecyloxy-2-(4-undecylphenyl)pyrimidine
5-teteadecyloxy-2-(4-dodecylphenyl)pyrimidine
5-tetradecyloxy-2-(4-tridecylphenyl)pyrimidine
5-tetradecyloxy-2-(4-tetradecylphenyl)pyrimidine
5-pentadecyloxy-2-(4-butylphenyl)pyrimidine
5-pentadecyloxy-2-(4-pentylphenyl)pyrimidine 5-pentadecyloxy-2-(4-hexylphenyl)pyrimidine

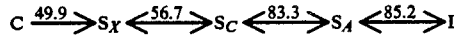

5-pentadecyloxy-2-(4-heptylphenyl)pyrimidine

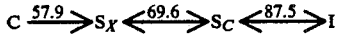

5-pentadecyloxy-2-(4-nonylphenyl)pyrimidine
5-pentadecyloxy-2-(4-decylphenyl)pyrimidine
5-pentadecyloxy-2-(4-undecylphenyl)pyrimidine
5-pentadecyloxy-2-(4-dodecylphenyl)pyrimidine
5-pentadecyloxy-2-(4-tridecylphenyl)pyrimidine
5-pentadecyloxy-2-(4-tetradecylphenyl)pyrimidine In the above-listed compounds, C, Sc, SA and I represent crystalline phase, smectic C phase, smectic A phase and isotropic liquid phase, respectively; Sx represents an unidentified smectic phase other than Sc phase, the liquid crystal molecule being tilted at the Sx phase; and numerals represent phase transition points (° C.).

The compound of the present invention is characterized by having smectic C liquid crystal phase. The smectic C liquid crystal phase is quite different from other smectic A, cholesteric or nematic phases with respect to a specific feature, the capability of developing ferroelectric properties by adding a suitable quantity of an optically active compound to a compound or a mixture exhibiting the above smectic C phase. Further, the Sc phase is present within the highest temperature region, among liquid crystal phases exhibiting or developing ferroelectric properties. In other words, as described above, liquid crystals having Sc phase are most important substances from the viewpoint of a component of ferroelectric liquid crystal materials, as compared with liquid crystals having other smectic phases at which the liquid crystal molecules are tilted.

West German patent publication No. DT 2257588 discloses a nematic liquid crystalline pyrimidine derivative expressed by the formula

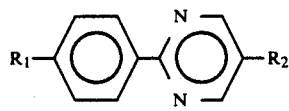

wherein R₁ and R₂ each represent an alkyl group or an alkoxy group each of 1 to 12 carbon atoms, and an electrooptical device having applied a nematic liquid crystal composition comprising the above derivative.

The formula expressing nematic pyrimidine derivatives disclosed in the above West German patent evidently includes a part of 5-alkoxy-2-(4-alkylphenyl)-pyrimidine compounds expressed by the formula (I). However, the compound concretely disclosed in the above DT patent is only one compound of the formula (I) wherein $R^1$ represents n—$C_6H_{13}$— and $R^2$ represents n—$C_4H_9$—, and the DT patent does not clearly state its smectic phases. In addition, in "Flüssige Kristalle in Tabellen II (1984), issued later, wherein the report of the inventors of the above DT patent is described, the following concrete three compounds are listed:

5-butoxy-2-(4-hexylphenyl)pyrimidine (Compound A)
5-hexyloxy-2-(4-butylphenyl)pyrimidine (Compound B)
5-hexyloxy-2-(4-hexylphenyl)pyrimidine (Compound C)

|  | Phase transition points | | | |
|---|---|---|---|---|
|  | C | S_A | N | I |
| Compound A | • 40 | • 56.5 | • 60.5 | • |
| Compound B | • 42 | • 72 | — | • |
| Compound C | • 45 | • 75 | — | • |

In view of the results of this report, it has been considered that the presence of Sc phase in the compound having the core structure of the formula (I) might not be expected.

Whereas, during extensive research made by the present inventors on Sc phase liquid crystals having a low viscosity, surprisingly enough we have found that a number of compounds exhibiting a Sc phase are present among compounds of the formula (I) wherein the linear alkyl group at the terminal thereof has a large number of carbon atoms, and have completed the present invention.

When the smectic C liquid crystalline 5-alkoxy-2(4-alkylphenyl)pyrimidine of the present invention alone or in the form of a smectic C mixture consisting of a plurality of the pyrimidines is mixed with at least one optically active compound, it is possible to constitute a ferroelectric liquid crystal material, and the resulting chiral smectic C liquid crystal material has a very high response rate.

This will be directly illustrated by reference examples described later. Namely, a ferroelectric liquid crystal material consisting of the smactic C liquid crystal compound of the present invention and an optically active compound exhibits a response rate which is as high as about three times that of a ferroelectric liquid crystal material consisting of a 5alkyl-2-(4-alkoxyphenyl)-pyrimidine expressed by the formula

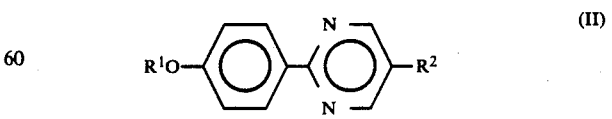

wherein $R^1$ and $R^2$ each represent an alkyl group of 1 to 18 carbon atoms, which pyrimdine is a smectic C liquid crystal having a low viscosity so far used, and an optically active compound. This fact has been found by Terashima et al for the first time, and they have prepared for the first time a superior smectic C liquid crystal mixture containing the smectic C liquid crystalline 5-alkoxy-2-(4-alkylphenyl)pyrimidine compound of the formula (I) as a component thereof and a ferroelectric liquid crystal material containing the above mixture and exhibiting superior response properties (Japanese patent application No. Sho 62-137883/1987).

The present invention provides a novel smectic C liquid crystal compound and when this smectic liquid crystal compound is used together with an optically active compound, a ferroelectric liquid crystal material having improved response properties is provided.

The present invention will be described in more detail by way of examples.

In addition, a part of the compounds of the present invention prepared in the same manner as in examples are already shown above together with their phase transition points.

Further, in reference examples described later, comparison of the compound of the present invention with conventional smectic C liquid crystal in ferroelectric liquid crystal materials containing these is shown.

Example 1

Preparation of 5-octyloxy-2-(4-octylphenyl)pyrimidine (a compound of the formula (I) wherein $R^1=n-C_8H_{17}-$ and $R^2=n-C_8H_{17}-$)

(i) Preparation of 4,6-dihydroxy-5-methoxy-2-(4-octylphenyl)pyrimidine

Metal sodium (23.4 g, 1.02 mol) was added to methanol (500 ml) to obtain sodium methoxide, followed by adding thereto 4-octylbenzamidine hydrochloride (84 g, 0.31 mol) and dimethyl methoxymalonate (55 g, 0.31 mol), refluxing the mixture for 8 hours, pouring the reaction mixture in acetic acid (500 ml), filtering off deposited crystals, washing them with water and drying to obtain 4,6-dihydroxy-5-methoxy-2-(4-octylphenyl)pyrimidine (91.5 g).

(ii) Preparation of 4,6-dichloro-5-methoxy-2-(4-octylphenyl)pyrimidine

To 4,6-dihydroxy-5-methoxy-2-(4-octylphenyl)pyrimidine (91.5 g, 0.28 mol) were added phosphorus oxychloride (258 g, 1.68 mol) and N,N-diethylaniline (46 g, 0.31 mol), followed by refluxing the mixture for 30 hours, distilling off excess phosphorus oxychloride under reduced pressure, dissolving the residue in toluene, sufficiently washing the solution with 2N-NaOH aqueous solution, further washing it with water, distilling off toluene and recrystallizing the residue from a mixed solvent of ethanol (280 ml) with ethyl acetate (10 ml) to obtain 4,6-dichloro-5-methoxy-2-(4-octylphenyl)pyrimidine in the form of colorless acicular crystals (74.2 g) (m.p.: 36.8–37.9° C.).

(iii) Preparation of 5-methoxy-2-(4-octylphenyl)pyrimidine

To 4,6-dichloro-5-methoxy-2-(4-octylphenyl)pyrimidine (74.2 g, 0.202 mol) were added ethanol (310 ml), water (15.5 ml), 5% Pd-activated carbon (5.7 g) and triethylamine (61.3 g, 0.606 mol), followed by agitating the mixture at about 40° C. in hydrogen current, filtering off the Pd-activated carbon adding toluene, sufficiently washing the mixture with 2N-NaOH aqueous solution, further washing it with water, distilling off toluene and recrystallizing the residue from ethanol (70 ml) to obtain 5-methoxy-2-(4-octylphenyl)pyrimidine in the form of colorless acicular crystals (54.9 g) having a m.p. of 40.1–41.8° C.

(iv) Preparation of 5-hydroxy-2-(4-octylphenyl)pyrimidine

To 5-methoxy-2-(4-octylphenyl)pyrimidine (53.9 g, 0.18 mol) were added diethylene glycol (500 ml) and NaOH (43.4 g, 1.08 mol), followed by agitating the mixture at about 200° C. for 2 hours, pouring the resulting material in acetic acid (700 ml), collecting deposited crystals and recrystallizing the crystals from a mixed solvent of heptane (100 ml) with ethyl acetate (10 ml) to obtain 5-hydroxy-2-(4-octylphenyl)pyrimidine (45.2 g) (m.p.: 147.3–148.7 ° C.).

(v) Preparation of the captioned compound

To 5-hydroxy-2-(4-octylphenyl)pyrimidine (5 g, 0.018 mol) were added ethanol (50 ml), octyl iodide (12.6 g, 0.053 mol) and diazabicyclo[5.4.0]undec-7-ene (0.053 mol), followed by refluxing the mixture for 4 hours, dissolving the reaction mixture in toluene, sufficiently washing the solution with 2N-NaOH aqueous solution, further washing it with water, distilling off toluene and recrystallizing the residue from methanol (75 ml) to obtain 5-octyloxy-2-(4-octylphenyl)pyrimidine (5 g). This product exhibited liquid crystalline properties and its phase transition points were as follows:

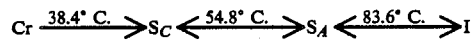

Reference example 1

A mixture consisting of 5-octyloxy-2-(4-hexylphenyl)pyrimidine as a compound of the present invention (80% by weight) and a compound (A) expressed by the formula

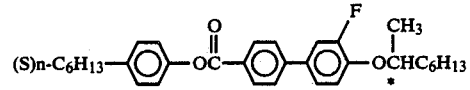

(20% by weight) i.e. a composition A exhibited the following phase transition points:

and crystallized at 5° C. This composition A was filled in a cell of 2 m thickness provided with transparent electrodes each obtained by coating the surface with PVA (polyvinyl alcohol) as an aligning agent and rubbing the resulting surface to subject it to a parallel aligning treatment, followed by placing the resulting element between two crossed polarizers and impressing an electric field thereto. As a result of impressing ±10V, change in the intensity of transmitted light was observed. The response time was sought from the change in the intensity of transmitted light at that time and the spontaneous polarization value Ps was sought according to Sawyer-Tower method. The results were as follows:

| Temperature (°C.) | Response time (μsec) | Ps (nC/cm$^2$) |
| --- | --- | --- |
| 40 | 40 | 9.4 |
| 30 | 50 | 12.3 |
| 20 | 70 | 14.7 |

Reference example 2

A mixture of a known compound, 5-octyl-2-(4-hexyloxyphenyl)pyrimidine (80% by weight) with the above-mentioned compound (A) (20% by weight) i.e. a composition B exhibited the following phase transition points:

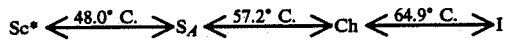

and crystallized at 10° C.

The reponse time and Ps of the composition B were sought. The results were as follows:

| Temperature (°C.) | Response time (μsec) | Ps (nC/cm$^2$) |
|---|---|---|
| 40 | 105 | 3.8 |
| 30 | 145 | 4.7 |
| 20 | 220 | 4.7 |

As described above, when the compound of the formula (I) as a smectic base compound is compared with the compound of the above formula (II), the Fs of the composition containing the compound of the formula (I) can be raised up to about three times that of the comPosition containing the compound of the formula (II); the response time is accordingly shortened down to about ⅓. Thus it is seen that the compound of the present invention has a notable function.

What we claim is:

1. A smectic liquid crystalline 5-alkoxy- 2-(4-alkylphenyl)pyrimidine compound expressed by the formula

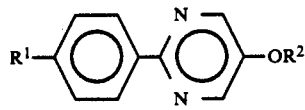

wherein $R^1$ represents a linear alkyl group of 4 to 20 carbon atoms and $R^2$ represents a linear alkyl group of 7 to 20 carbon atoms.

2. A smectic liquid crystalline 5-alkoxy-2-(4-alkylphenyl)pyrimidine compound according to claim 1, wherein in the formula (I), $R^1$ is a linear alkyl group of 6 to 15 carbon atoms and $R^2$ is a linear alkyl group of 7 to 15 carbon atoms.

3. A smectic liquid crystalline 5-alkyl-2-(4-alkylphenyl)pyrimidine compound according to claim 1, wherein in the formula (I), $R^1$ is a linear alkyl group of 6 to 12 carbon atoms and $R^2$ is a linear alkyl group of 7 to 15 carbon atoms.

4. A smectic liquid crystal 5-alkoxy-2-(4-alkylphenyl)pyrimidine compound according to claim 1, wherein said compound is selected from the group consisting of
5-heptyloxy-2-(4-hexylphenyl)pyrimidine
5-heptyloxy-2-(4-heptylphenyl)pyrimidine
5-heptyloxy-2-(4-octylphenyl)pyrimidine
5-octyloxy-2-(4-hexylphenyl)pyrimidine
5-octyloxy-2-(4-heptylphenyl)pyrimidine
5-octyloxy-2-(4-octylphenyl)pyrimidine
5-octyloxy-2-(4-nonylphenyl)pyrimidine
5-octyloxy-2-(4-decylphenyl)pyrimidine
5-nonyloxy-2-(4-hexylphenyl)pyrimidine
5-nonyloxy-2-(4-heptylphenyl)pyrimidine
5-nonyloxy-2-(4-octylphenyl)pyrimidine
5-nonyloxy-2-(4-nonylphenyl)pyrimidine
5-nonyloxy-2-(4-decylphenyl)pyrimidine
5-decyloxy-2-(4-hexylphenyl)pyrimidine
5-decyloxy-2-(4-heptylphenyl)pyrimidine
5-decyloxy-2-(4-octylphenyl)pyrimidine
5-decyloxy-2-(4-nonylphenyl)pyrimidine
5-decyloxy-2-(4-decylphenyl)pyrimidine
5-undecyloxy-2-(4-hexylphenyl)pyrimidine
5-undecyloxy-2-(4-heptylphenyl)pyrimidine
5-undecyloxy-2-(4-octylphenyl)pyrimidine
5-undecyloxy-2-(4-nonylphenyl)pyrimidine
5-undecyloxy-2-(4-decylphenyl)pyrimidine
5-dodecyloxy-2-(4-hexylphenyl)pyrimidine
5-dodecyloxy-2-(4-heptylphenyl)pyrimidine
5-dodecyloxy-2-(4-octylphenyl)pyrimidine
5-dodecyloxy-2-(4-nonylphenyl)pyrimidine
5-dodecyloxy-2-(4-decylphenyl)pyrimidine
5-tridecyloxy-2-(4-hexylphenyl)pyrimidine
5-tridecyloxy-2-(5-oxtylphenyl)pyrimidine
5-tridecyloxy-2-(4-nonylphenyl)pyrimidine
5-tetradecyloxy-2-(4-hexylphenyl)pyrimidine
5-tetradecyloxy-2-(4-octylphenyl)pyrimidine
5-pentadecyloxy-2-(4-hexylphenyl)pyrimidine and
5-pentadecyloxy-2-(4-octylphenyl)pyrimidine.

* * * * *

UNITED STATES PATENT AND TRADEMARK OFFICE
CERTIFICATE OF CORRECTION

PATENT NO. : 4,906,400
DATED : March 6, 1990
INVENTOR(S) : Saito et al.

It is certified that error appears in the above-identified patent and that said Letters Patent is hereby corrected as shown below:

In column 1, item [56], the following references should be listed under the heading "FOREIGN PATENT DOCUMENTS":

--2164702      8/1972      France
  206228      12/1986      European Pat. Off.--.

Column 12, line 41, change "5-tridecyloxy-2-(5-oxtylphenyl) pyrimidine" to --5-tridecyloxy-2-(5-octylphenyl)pyrimidine--.

Signed and Sealed this

Third Day of September, 1991

Attest:

HARRY F. MANBECK, JR.

*Attesting Officer*      *Commissioner of Patents and Trademarks*